United States Patent [19]

Meyer-Simon et al.

[11] 3,978,103
[45] Aug. 31, 1976

[54] SULFUR CONTAINING ORGANOSILICON COMPOUNDS

[75] Inventors: Eugen Meyer-Simon; Werner Schwarze, both of Frankfurt; Friedrich Thurn, Grossauheim; Rudolf Michel, Somborn, all of Germany

[73] Assignee: Deutsche Gold- und Silber-Scheideanstalt vormals Roessler, Germany

[22] Filed: May 6, 1974

[21] Appl. No.: 467,583

Related U.S. Application Data

[62] Division of Ser. No. 277,043, Aug. 1, 1972, Pat. No. 3,842,111.

[30] Foreign Application Priority Data

Aug. 17, 1971 Germany............................ 2141159
Aug. 17, 1971 Germany............................ 2141160
Mar. 14, 1972 Germany............................ 2212239

[52] U.S. Cl................... 260/448.8 R; 260/448.2 N; 260/82.3; 260/83.7; 260/85.3 C; 260/33.6 AQ; 260/42.15; 260/42.32; 260/42.33; 260/42.36; 260/42.44; 260/42.47; 260/42.49; 260/763; 260/765; 260/766; 106/308 Q; 152/330 R; 526/20; 526/29; 526/30; 526/339; 526/340

[51] Int. Cl.².......................................... C07F 7/18

[58] Field of Search............... 260/448.8 R, 448.2 N

[56] References Cited

UNITED STATES PATENTS

| | | | |
|---|---|---|---|
| 3,255,140 | 6/1966 | Sinn et al. | 260/448.8 R X |
| 3,344,161 | 9/1967 | Moedritzer et al. | 260/448.8 R |
| 3,530,160 | 9/1970 | Gardner et al. | 260/448.8 R X |
| 3,686,326 | 8/1972 | Oswald et al. | 260/448.2 N X |
| 3,768,537 | 10/1973 | Hess et al. | 260/448.8 R X |

OTHER PUBLICATIONS

Schmidt et al., "Inorganic Chemistry", 4, 1962, pp. 909–912.
Schmidt et al., "Ber.", 94, pp. 1426–1432, (1961).
Nasiak et al., "J. Org. Chem.", 24, 1959, pp. 492–496.
Gornowicz et al., "Mechanisms of Reactions of Sulphur Compounds", 3, 1968, pp. 53–56.
Reid, "Organic Chemistry of Bivalent Sulfur", 1, 1958, p. 126.

*Primary Examiner*—Paul F. Shaver
*Attorney, Agent, or Firm*—Cushman, Darby & Cushman

[57] ABSTRACT

Sulfur containing organosilicon compounds are prepared having the formula:

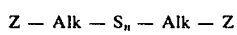

$$Z - Alk - S_n - Alk - Z$$

in which Z is:

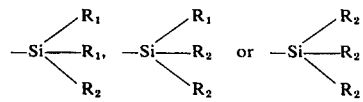

where $R_1$ and R alkyl of 1 to 4 carbon atoms or phenyl and $R_2$ is alkoxy of 1 to 8 carbon atoms, cycloalkoxy of 5 to 8 carbon atoms or alkylmercapto of 1 to 8 carbon atoms, alk is a divalent aliphatic hydrocarbon or unsaturated aliphatic hydrocarbon or a cyclic hydrocarbon containing 1 to 18 carbon atoms and n is a whole number from 2 to 6.

28 Claims, No Drawings

SULFUR CONTAINING ORGANOSILICON COMPOUNDS

This is a division of Application Ser. No. 277,043 filed Aug. 1, 1972, now U.S. Pat. No. 3,842,111.

The present invention is directed to new sulfur containing organosilicon compounds which are useful for example as bonding agents in sulfur vulcanizable rubber mixtures reinforced with natural or synthetic silica. The rubber can be natural rubber or other sulfur vulcanizable rubbers such as butadiene-styrene, butadiene-acrylonitrile, polyisoprene, polybutadiene, ethylene-propylene-diene terpolymer and butyl rubber.

The invention is also concerned with processes for producing the novel compounds.

The compounds of the invention are also useful as intermediate products for producing water repellant agents or oxidation inhibitors or as protective agents for metal surfaces.

It is known to use 3-mercaptopropyl trimethoxysilane as adhesive promotors in rubber mixtures. Advantageously, however, in the use of such compounds it is important that they reduce the strength of the raw mixture and considerably raise the tensile strength of the vulcanizate and definitely raise the rebound and shore hardness. On the contrary the processing properties of the mixture are disadvantageously influenced, for example the prevulcanization time is greatly reduced. This means a reduction of the processing safety. Furthermore, the Defo elasticity is greatly increased which means an increase in the elastic rubber portion of the raw mixture and has as a consequence an increased difficulty in their further processing, for example in injection molding.

It is an object of the invention to prepare new sulfur containing organosilicon compounds which can be used for this purpose without requiring that allowance be made for the above named disadvantages. On the one hand they substantially produce the advantages for example of 3-mercaptopropyltrimethoxysilane but on the other hand substantially more favorably effect the processing properties of the rubber-filler mixture. Furthermore, many of the compounds of the invention, because of their simple method of production with good yields and the easy availability of their starting materials, are accessible in very economical manners. Therefore these compounds are excellent for industrial duty.

The new compounds have the general formula:

I Z — alk — $S_n$ — alk — Z in which Z is:

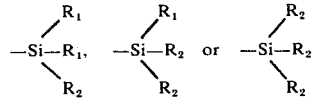

and in which $R_1$ is an alkyl group of 1 to 4 carbon atoms or phenyl and $R_2$ is an alkoxy group with 1 to 8, preferably 1 to 4, carbon atoms, a cycloalkoxy group with 5 to 8 carbon atoms or a straight or branched chain alkylmercapto group with 1 to 8 carbon atoms. All the $R_1$ and $R_2$ groups can be the same or different. Alk is a divalent hydrocarbon group with 1 to 18 carbon atoms. It can be straight or branched chain and can be a saturated aliphatic hydrocarbon group, an unsaturated aliphatic hydrocarbon group or a cyclic hydrocarbon group. Preferably alk has 1 to 6, most preferably 2 or 3 carbon atoms and $n$ is a whole number of 2 to 6, especially 2, 3 or 4, most preferably 4.

The compounds of the invention are valuable bonding agents (adhesion promotors) which are added with advantage, for example in vulcanizable or cross linkable rubber mixtures reinforced with finely divided light or white fillers, especially natural or synthetic silica fillers. There can also be used other known metaloxides such as magnesium oxide and aluminum oxide, mixtures of oxides and mixed oxides, silicates, e.g. glass, glass fibers, etc. There can also be present carbon black as a strengthening filler.

The new rubber adjuvants improve the mechanical properties of the vulcanizate, especially in static and dynamic stress.

Especially suitable for this purpose are compounds in which the alk is an ethylene or propylene group (trimethylene) and Z is the group

where $R_2$ is alkoxy of 1 to 4 carbon atoms.

The compounds in which $R_2$ is alkoxy are preferred to those in which $R_2$ is an alkyl mercapto group.

The compounds of the type set forth in general are yellow liquids which cannot be distilled without decomposition. Their viscosities depend upon the chain length of the alkylene group, i.e. the viscosity increases with increasing molecular weight.

Examples of compounds within the invention include 3,3'-bis (trimethoxysilylpropyl) disulfide, 3,3'-bis(triethoxysilylpropyl) tetrasulfide, 3,3'-bis(trimethoxysilylpropyl) tetrasulfide, 2,2'-bis (triethoxysilylethyl) tetrasulffide, 3,3'-bis(trimethoxysilylpropyl) trisulfide, 3,3'-bis(triethoxysilylpropyl) trisulfide, 3,3'-bis(tributoxysilylpropyl) disulfide, 3,3'-bis(trimethoxysilylpropyl) hexasulfide, 3,3'-bis(trioctoxysilylpropyl) tetrasulfide, 3,3'-bis(trihexoxysilylpropyl) disulfide, 3,3'-bis(tri-2''-ethylhexoxysilylpropyl) trisulfide, 3,3'-bis triisooctoxysilylpropyl) tetrasulfide, 3,3'-bis(tri t-butoxysilylpropyl) disulfide, 2,2'-bis(methoxy diethoxy silyl ethyl) tetrasulfide, 2,2'-bis (tripropoxysilylethyl) pentasulfide, 3,3'-bis (tricyclohexoxysilylpropyl) tetrasulfide, 3,3'-bis(tricyclopentoxysilylpropyl) trisulfide, 2,2'-bis(tri-2''-methylcyclohexoxysilylethyl) tetrasulfide, bis(trimethoxysilylmethyl) tetrasulfide), 3,3'-bis (trimethylmercaptosilylpropyl) tetrasulfide, 2,2'-bis(triethylmercaptosilylethyl) disulfide, 2,2'-bis(tributylmercaptosilylethyl) trisulfide, 2,2'-bis(tri sec. butylmercaptosilylethyl) trisulfide, 3,3'-bis (trioctylmercaptosilylpropyl) tetrasulfide, 2,2'-bis (trihexylmercaptosilylethyl) hexasulfide, 3,3'-bis (ethyldipropylmercaptosilylpropyl) tetrasulfide, 3-methoxy ethoxy propoxysilyl 3'-diethoxybutoxysilylpropyltetrasulfide, 2,2'-bis (dimethyl methoxysilylethyl) disulfide, 2,2'-bis(dimethyl sec.butoxysilylethyl) trisulfide, 3,3'-bis (methyl butylethoxysilylpropyl) tetrasulfide, 3,3'-bis(di t-butylmethoxysilylpropyl) tetrasulfide, 2,2'-bis (phenyl methyl methoxysilylethyl) trisulfide, 3,3'-bis (diphenyl isopropoxysilylpropyl) tetrasulfide, 3,3'-bis(- diphenyl cyclohexoxysilylpropyl) disulfide, 3,3'-bis(-dimethyl ethylmercaptosilylpropyl) tetrasulfide, 2,2'-bis(methyl dimethoxysilylethyl) trisulfide, 2,2'-bis(-methyl ethoxypropoxysilylethyl) tetrasulfide, 3,3'-bis(-diethyl methoxysilylpropyl) tetrasulfide, 3,3'-bis (ethyl di-sec. butoxysilylpropyl) disulfide, 3,3'-bis(propyl diethoxysilylpropyl) disulfide, 3,3'-bis(butyl dimethoxysilylpropyl) trisulfide, 3,3'-bis(phenyl dimethoxysilylpropyl) tetrasulfide, 3-phenyl ethoxybutoxysilyl 3'-trimethoxysilylpropyl tetrasulfide, 4,4'-bis(trimethoxysilylbutyl) tetrasulfide, 6,6'-bis (triethoxysilylhexyl) tetrasulfide, 12,12'-bis(triisopropoxysilyl dodecyl) disulfide, 18,18'-bis(trimethoxysilyloctadecyl)tetrasulfide, 18,18'-bis (tripropoxysilyloctadecenyl) tetrasulfide, 4,4'-bis(trimethoxysilyl-buten-2-yl) tetrasulfide, 4,4'-bis (trimethoxysilylcyclohexylene) tetrasulfide, 5,5'-bis(dimethoxy methylsilylpentyl) trisulfide, 3,3'-bis(trimethoxysilyl-2-methyl propyl) tetrasulfide, 3,3'-bis(dimethoxyphenylsilyl-2-methylpropyl) disulfide.

The compounds of the invention can be prepared in a simple and economical manner by reacting 2 moles of a compound of the formula II  Z — alk — hal where hal is a chlorine, bromine or iodine atom (i.e. halogen of atomic weight 35 to 127) and Z and alk are as defined above, with 1 mole of a compound of the formula III  $Me_2 S_n$ where Me is ammonium or a metal atom, especially an alkali metal atom, e.g. potassium, sodium, rubidium or cesium and $n$ is as defined above. Preferably Me is sodium. The reaction is preferably carried out in an organic solvent, the product is separated from the halide material formed and in a given case the organic solvent removed.

Examples of suitable starting compounds within formula III are $Na_2S_5$, $K_2S_6$, $Na_2S_6$, $Cs_2 S_6$, $K_2S_4$, $K_2S_2$, $K_2S_3$, $(NH_4)_2S_2$, $(NH_4)_2S_3$, $(NH_4)_2S_4$ and especially $Na_2S_2$, $Na_2S_3$ and $Na_2S_4$.

Other polysulfides which can be used include alkaline earth metal polysulfides, e.g. $BaS_3$ and $BaS_4$.

The mole ratio of the compound of formula II to the compound of formula III can vary from 2 to 1 to 2 to 2.

Typical examples of starting materials within formula II are 2-chloroethyl trimethoxysilane, 2-bromoethyl trimethoxysilane, 2-iodoethyl trimethoxy silane) 3-bromopropyl trimethoxysilane, 3-chloropropyl trimethoxysilane, 3-iodopropyl trimethoxysilane, 3-bromopropyl triethoxysilane, 3-iodopropyl triethoxysilane, 2-bromoethyl tripropoxysilane, 2-iodoethyl tributoxysilane, 2-chloroethyl tri sec.butoxysilane, 3-bromopropyl tri-t-butoxysilane, 3-iodopropyl triisopropoxysilane, 3-bromopropyl trioctoxysilane, 2-chloroethyl tri-2'-ethylhexoxysilane, 2-bromoethyl dimethoxy ethoxysilane, 3-iodopropyl methoxyethoxypropoxysilane, 3-chloropropyl dimethoxy methylsilane, 3-bromopropyl dimethoxy methylsilane, 3-chloropropylmethoxydimethylsilane, 3-bromopropylmethoxydimethylsilane, 3-chloropropyldimethoxymethylmercaptosilane, 3-iodopropyldimethoxymethylmercaptosilane, 3-chloropropyl methoxy di (methylmercapto) silane, 3-iodopropyl methoxy di (methylmercapto) silane, 3-chloropropyl methoxy methyl methylmercapto silane, 3-bromopropyl methoxy methyl methylmercapto silane, 3-iodopropyl methoxy methyl methylmercapto silane, 2-chloroethyl trimethylmercaptosilane, 3-bromoethyl trimethylmercaptosilane, 2-iodoethyl triethylmercaptosilane, 2-bromoethyl triisopropylmercaptosilane, 3-iodopropyl tripropylmercaptosilane, 3-chloropropyl tributylmercaptosilane, 2-bromoethyl tri sec. butylmercaptosilane, 3-bromopropyltrioctylmercaptosilane, 3-chloropropyl cyclohexoxy dimethylsilane, 3-bromopropyl cyclohexoxy dimethylsilane, 4-chlorobutyl trimethoxysilane, 4-bromobutyltrimethoxysilane, 3-chloro-3-methylpropyl trimethoxysilane, 3-bromo-3-methylpropyl trimethoxysilane, 3-chloro-3-methylpropyl tripropoxysilane, 3-bromo-3-methylpropyl tripropoxysilane, 3-chloro-3-ethylpropyldimethoxy methylsilane, 3-bromo-3-ethylpropyldimethoxy methylsilane, 3-chloro-2-methylpropyl trimethoxysilane, 3-bromo-2-methylpropyl trimethoxysilane, 3-chloro-2-methylpropyl dimethoxy phenylsilane, 3-bromo-2-methylpropyl dimethoxy phenylsilane, 3-chlorocyclohexyl-trimethoxysilane, 3-iodocyclohexyltrimethoxysilane, 3-chlorocyclohexyl dimethoxy propylmercaptosilane, 3-iodocyclohexyl-dimethoxy propylmercaptosilane, 12-chlorododecyl trimethoxysilane, 12-iodododecyl trimethoxysilane, 12-chlorododecyl triethoxysilane, 12-iodododecyl triethoxysilane, 18-chlorooctadecyl trimethoxysilane, 18-bromooctadecyl trimethoxysilane, 18-chlorooctadecyl methoxydimethylsilane, 18-bromooctadecyl methoxydimethylsilane, 2-chloro-2-methylethyl-trimethoxysilane, 2-iodo-2-methylethyl-trimethoxysilane, 2-chloro-2-methylethyl-triethoxysilane, 2-iodo-2-methylethyltriethoxysilane, 2-chloro-2-methylethyl-tripropoxysilane, 2-iodo-2-methylethyl-tripropoxysilane, 2-chloro-2-methylethyl-trioctyloxysilane, and 2-iodo-2-methylethyl-trioctyloxysilane.

Of the sulfur containing organosilicon compounds within formula I preferably there are prepared 3,3'-bis (trimethoxy or triethoxy silylpropyl) sulfides, specifically di, tri and tetrasulfides. Other compounds of the invention employed with good success include the 2,2'-bis(trimethoxy, triethoxy, tri-methylethoxy, tributoxy, etc. silylethyl) sulfides, preferably the di, tri and tetrasulfides, as well as the 3,3'-bis (trimethoxy or dimethoxy methylsilylisobutyl) sulfides, especially the di, tri and tetrasulfides, and also the 4,4'-bis (trimethoxy or dimethoxyphenyl or dimethoxymethylmercapto, or methoxydimethyl silylbutyl) sulfides, especially the di, tri and tetrasulfides. The compounds of formula II are preferably chloro or bromo compounds and alk is preferably di, tri or tetra methylene, in a given case lower alkyl substituted derivatives thereof, especially methyl substituted.

The temperature at which the reaction is carried out between the compound of formula II and the compound of formula III is not critical. The reaction can take place at room temperature as well as temperatures below room temperature. In order to increase the speed of reaction, however, it is generally advantageous to work at elevated temperatures up to the boiling point of the solvent used in a given case. Since the starting materials are liquid the reaction can take place in the absence of a solvent. Advantageously, however, there is used an inert organic solvent, most preferably volatile organic solvent, which is able to partially or more preferably completely dissolve the compound of formula III. Desirably the solvent does not dissolve the metal halide formed. Solvents include for example aliphatic an cycloaliphatic alcohols such as methyl alcohol, ethyl alcohol, propyl alcohol, isopropyl alcohol, butyl alcohol, sec. butyl alcohol, t-butyl alcohol, amyl alcohol, hexyl alcohol, octyl alcohol, 2-ethylhexyl alcohol, isooctyl alcohol, cyclohexanol, cyclopentanol, methylcyclohexanol. Preferably there is used an alcohol which corresponds to the structure and number of carbon atoms in the hydroxycarbonoxy group bonded to the silicon, for example ethyl alcohol with ethoxy group containing silanes. There also can be used ketones containing up to eight carbon atoms such as acetone, methyl ethyl ketone, methyl propyl ketone, methyl isopropyl ketone, methyl butyl ketone, diethyl ketone, methyl hexyl ketone and cyclohexanone. There also can be used cyclic ethers such as tetrahydrofurane, dioxane, dioxolane and other oxygen containing compounds. The preferred solvents are methyl alcohol, ethyl alcohol, propyl alcohol, isopropyl alcohol, cyclohexyl alcohol and acetone.

Furthermore it has been found advantageous to carry out the reaction with the exclusion of water and/or the exclusion of air. As inert gases there can be used noble gases, e.g. argon, neon and helium, or nitrogen. Both precautions effect a reduction in side reactions.

In carrying out the process of the invention it is more preferable to first dissolve the compound of formula III partially or completely in an inert organic solvent. The solvent is advantageously selected so that undesired ester interchanges of the silicon atom are excluded. To this solution there is added the starting material of formula II, in a given case likewise dissolved in a solvent. After the end of the reaction the salt (metal halide) separated out is filtered off and the organic solvent, in a given case under reduced pressure, is removed by distillation. The end product cannot be distilled without decomposition. It remains behind in the distillation sump. It can be used directly without purification.

It was completely surprising that the process set forth above could be used with starting compounds which have the halogen atom in the beta position. It is known from Organometallic Reviews A 6 (1970) 2, pages 153-207, that halogen atoms, for example chlorine or bromine atoms which are found in the beta position to the silicon atom, are unstabile. For this reason substitution reactions in the presence of specific solvents, for example alcoholic alkalis, as sodium methylate solution, are practically impossible since a splitting of the Si-C-bond takes place quickly. Thus, for example, it is known that organosilicon compounds, as β-chloroethyltriethylsilane are substantially less stable to alkali metal hydroxide or alkoxide solutions than are the corresponding alpha or gamma isomers. For example β-chloroethyltriethylsilane is quickly decomposed with the quantitative formation of ethylene and the setting free of chloride ions when using aqueous or alcoholic alkali metal hydroxide or alkoxide solutions. The process of the invention on the contrary can also be carried out in the substitution reactions with addition of organosilicon compounds which contain a halogen atom in beta position to the silicon atom. In view of this state of the art it was unexpected and surprising that contrary to the expected splitting a substitution occurs.

The reaction process can also be carried out continuously.

In a suitable working of the process both reaction partners are preheated separately in the liquid phase. In addition the sulfide of formula III is brought into solution, for example in alcoholic solution.

Then the reaction partners are fed into a heatable reaction vessel and allowed to react with each other while flowing through the vessel. It is advantageous for this purpose to use a tubular reaction vessel provided with a heating jacket and filled with packing, for example Raschig rings or similar known packing.

The reaction temperature is usually between about 30° and 120°C., especially between about 60° and 110°C., preferably at about the boiling point of the solvent. As previously pointed out the temperature can be below 30°C. and by the addition of higher boiling solvents or by working under superatmospheric pressure in a given case can be above 120°C.

The mixture of the resulting compounds then flows through a cooling aggregate whereupon the filtering off of the solid constituents takes place, for example over a Seitz filter, and the rectification in a vacuum for the removal of solvent.

There can be produced in another simple manner compounds of formula I in which $n$ is 3 to 6 by reacting (a) 2 moles of a compound of the formula IV Z-alk-SH, in which Z and alk are as defined above with 1 mole of a compound of the formula V $S_mHal_2$, in which Hal is a chroline or bromine atom (i.e. a halogen of atomic weight 35 to 80), and $m$ is a whole number of 1 to 4. Compounds within formula V include $SCl_2$, $SBr_2$, $S_2Cl_2$, $Sr\ Br_2$, $S_3Cl_2$, $S_2Br_2$, $S_4Cl_2$ and $S_4Br_2$.

Compounds within formula IV are 2-mercaptoethyl trimethoxysilane, 3-mercaptopropyl trimethoxysilane, 3-mercaptopropyl triethoxysilane, 2-mercaptoethyl tripropoxysilane, 2-mercaptoethyl tri sec. butoxysilane, 3-mercaptopropyl tri-t-butoxysilane, 3-mercaptopropyl triisopropoxysilane, 3-mercaptopropyl trioctoxysilane, 2-mercaptoethyl tri 2'-ethylhexoxysilane, 2-mercaptoethyl dimethoxy ethoxysilane, 3-mercaptopropyl methoxyethoxypropoxysilane, 3-mercaptopropyl dimethoxy methylsilane, 3-mercaptopropyl methoxy dimethylsilane, 3-mercaptopropyl dimethoxy methylmercaptosilane, 3-mercaptopropyl methoxy di(methylmercapto) silane, 3-mercaptopropyl methoxy methyl methylmercapto silane, 2-mercaptoethyl trimethylmercaptosilane, 2-mercaptoethyl triethylmercaptosilane, 2-mercaptoethyl triisopropylmercapto silane, 3-mercaptopropyl triisopropylmercapto silane, 3-mercaptopropyl tributylmercapto silane, 2-mercaptoethyl tri-sec.-butylmercaptosilane, 3-mercaptopropyl trioctylmercaptosilane, 3-mercaptopropyl cyclohexoxy dimethyl silane, 4-mercaptobutyl trimethoxysilane, 3-mercapto-3-methylpropyltrimethoxysilane, 3-mercapto-3-methylpropyl-tripropoxysilane, 3-mercapto-3-ethylpropyl-dimethoxy methylsilane, 3-mercapto-2-methylpropyl trimethoxysilane, 3-mercapto-2-methylpropyl dimethoxy phenylsilane, 3-mercaptocyclohexyl-trimethoxysilane, 3-mercaptocyclohexyl dimethoxy propylmercaptosilane, 12-mercaptododecyl trimethoxy silane, 12-mercaptododecyl triethoxy silane, 18-mercaptooctadecyl trimethoxysilane, 18-mercaptooctadecyl methoxydimethylsilane, 2-mercapto-2-methylethyl-trimethoxysilane, 2-mercapto-2-methylethyl-triethoxysilane, 2-mercapto-2-methylethyl-tripropoxysilane, and 2-mercapto-2-methylethyl-trioctoxysilane, Preferably the reaction is carried out in the presence of an organic solvent and the hydrogen halide formed, as well as in a given case the solvent, removed.

Another procedure is (b) to oxidize a compound of formula IV, preferably at elevated temperature, e.g. 60° to 130°C. to a compound of formula I in which $n$ is 2, preferably in the presence of an organic solvent and in a given case unreacted starting compounds and solvent are removed from the reaction mixture.

It is recommended to carry out the reaction according to procedure (a) at room temperature. However, temperatures above and below this can be used, e.g. 0° to 80°C. By employing the higher temperatures a strong reaction must be reckoned with.

As stated it is advantageous to carry out the reaction in the presence of inert solvents. As such there can be used ethers, e.g. diethyl ether, dimethyl ether, dipropyl ether, methyl butyl ether, tetrahydrofurane, dioxane, aromatic hydrocarbons, for example benzene, toluene and xylene. Petroleum ether is a preferred solvent.

As in the previously described reactions it is preferred to carry out the reaction with the exclusion of water and/or with an inert atmosphere. For example, the reaction is carried out under nitrogen. This procedure avoids the formation of byproducts which would reduce the yield.

In carrying out process (a) one proceeds suitably by diluting the compound of formula IV for example with petroleum ether and then adds the compound V likewise diluted with petroleum ether. During the reaction suitably there is led through the mixture an inert gas, especially nitrogen. Leading through of the inert gas also takes place during the subsequent after reaction which should be held at the boiling temperature. The after reaction should take place until no more hydrogen halide gas escapes. After the end of the reaction the organic solvent is removed under reduced pressure. The compounds of the invention obtained by the process cannot be distilled without decomposition. They remain behind in the distillation sump.

In carrying out the process according to process (b) there can be used the oxidation agents known to oxidize mercaptans to disulfide set forth in Houben-Weyl "Methoden der Organischer Chemie", 4th edition, 1955 Vol. 9, pages 59 to 65, the entire disclosure of which is incorporated by reference. Thus there can be used oxygen, halogen of atomic weight 35 to 127, (i.e. chlorine, iodine or bromine), nitric oxide (NO), sulfuryl chloride ($SO_2Cl_2$). For maximum yield the oxidizing agent should be used in at least the stoichiometric amount. Preferably there are employed compounds of the formula VI $R_3SOR_4$, most preferably in excess. In formula VI $R_3$ and $R_4$ are the same or different and are alkyl of 1 to 6 carbon atoms, preferably methyl. Examples of such compounds include dimethyl sulfoxide, diethyl sulfoxide, dipropyl sulfoxide, dibutyl sulfoxide, diamyl sulfoxide, dihexyl sulfoxide, diisopropyl sulfoxide, di sec. butyl sulfoxide, methyl ethyl sulfoxide, methyl hexyl sulfoxide and ethyl propyl sulfoxide. The oxidation agent must be added under such conditions that a hydrolysis of bond between the silicon atom and $R_2$ does not take place. The reaction takes place preferably at temperatures above room temperature, although room temperature can be used. For example in using dialkyl sulfoxides, especially dimethyl sulfoxide, a temperature range of 0° to 120°C. is preferred.

This process also can be carried out in the presence of an organic solvent. For example there can be used aromatic hydrocarbon such as xylene, toluene and benzene. According to an especially preferred variant an excess of the dialkyl sulfoxide is used which can then function simultaneously as the solvent.

It is also recommended in this variant to work in an inert gas atmosphere. For example nitrogen can be led through the reaction solution whereby simultaneously the byproducts of formula VII $R_3SR_4$ can be removed. This can be converted again to starting compound VI by catalytic air oxidation which can again be used in the process.

The water formed besides in the reaction can remain in the reaction solution because it only effects a partial and therefore non disturbing hydrolysis of compounds produced. If desired it can be removed by an entraining distillation with toluene.

After the end of the reaction which can last about 5 to 24 hours the starting materials are removed by distillation which also can take place under reduced pressure. The compounds of the invention, as already mentioned, remain behind in the distillation sump. A purification is not necessary.

Unless otherwise indicated all parts and percentages are by weight.

EXAMPLE 1

There were gradually introduced into a boiling solution of 0.5 mole of $Na_2S_2$ in 500 ml of water free methyl alcohol 1 mole of 3-chloropropyl trimethoxysilane. After the end of the reaction the separated salt was filtered off and the filtrate freed from the solvent in a vacuum. There were obtained 171 grams (87.5% of theory) of the compound 3,3'-bis(trimethoxysilypropyl) disulfide of the formula

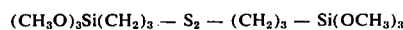

$(CH_3O)_3Si(CH_2)_3 - S_2 - (CH_2)_3 - Si(OCH_3)_3$

| Analytic values: | C | H | Si | S |
|---|---|---|---|---|
| calculated | 36.89 | 7.74 | 14.37 | 16.41 |
| found | 36.20 | 7.48 | 13.76 | 15.74 |

EXAMPLE 2

There were gradually added to a boiling solution of 0.5 mole of $Na_2S_4$ in 500 ml of waterfree ethanol 1 mole of 3-chloropropyl-triethoxysilane. After the end of the reaction the separated salt was removed by filtration and the filtrate freed from the solvent in a vacuum. There were obtained 263 grams (95.8% of theory) of the compound 3,3'-bis(triethoxysilylpropyl) tetrasulfide of the formula

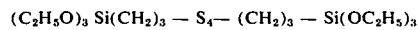

$(C_2H_5O)_3 Si(CH_2)_3 - S_4 - (CH_2)_3 - Si(OC_2H_5)_3$

| Analytical values: | C | H | Si | S |
|---|---|---|---|---|
| Calculated | 40.11 | 7.84 | 10.42 | 23.79 |
| Found | 40.0 | 7.78 | 10.48 | 22.98 |

EXAMPLE 3

There were gradually added to a boiling solution of 2 moles of $Na_2S_4$ in 2000 ml of water free methanol 4 moles of 3-chloropropyl trimethoxysilane. After the end of the reaction the separated salt was filtered off and the solvent removed in a vacuum. There were obtained 859 grams (94.1% of theory) of the compound 3,3'-bis(trimethoxysilylpropyl) tetrasulfide of the formula

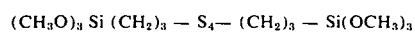

$(CH_3O)_3 Si (CH_2)_3 - S_4 - (CH_2)_3 - Si(OCH_3)_3$

| Analytical values: | C | H | Si | S |
|---|---|---|---|---|
| calculated | 31.69 | 6.65 | 12.35 | 28.20 |
| found | 31.20 | 6.43 | 12.40 | 27.35 |

EXAMPLE 4

There were gradually added to a solution of 0.5 mole of Na₂S₄ in 500 ml in water free ethanol at 50°C. 1 mole of 2-chloroethyltriethoxysilane. After the end of the reaction the separated salt was filtered off and the filtrate freed of the solvent in the vacuum. There were obtained 226.5 grams (88.7%) of theory of the compound 2,2'-bis(triethoxysilylethyl) tetrasulfide of the formula (C₂H₅O)₃Si — (CH₂)₂ — S₄— (CH₂)₂ — Si(OC₂H₅)₃

| Analytical values: | C | H | Si | S |
|---|---|---|---|---|
| calculated | 37.61 | 7.49 | 10.99 | 25.10 |
| found | 37.12 | 7.32 | 11.21 | 24.38 |

EXAMPLE 5

In two preheaters there were separately heated to about 70°C. 3-chloropropyltriethoxysilane and a solution of disodium tetrasulfide (Na₂S₄) in ethyl alcohol (1 mole in 1 liter of industrial pure, about 96% alcohol).

With the help of pumps (for example type HG of the firm Lewa in Leonberg at Stuttgart) there were fed into the flow through reactor from the preheaters always in the ratio of 2 moles of silane for each mole sulfide, i.e. for each liter of solution. The reaction was filled with Raschig rings and the fluid of the heating jacket was held at 100°C. The reaction time in the reaction was regulated (as flow through time) at about 15 minutes.

The reaction mixture passed through the after reactor during 5 minutes at which time the final temperature was 70°C. After the following cooling in a heat exchanger to about room temperature the precipitated solid sodium chloride was separated off with a filtering device and the ethyl alcohol distilled off in a vacuum at about 50° to 60°C. There was recovered the almost pure silyl compound.

The yield of 3,3'-bis (triethoxysilylpropyl)-tetrasulfide amounted to 95% of the theory.

EXAMPLE 6

In the same apparatus as in example 5 and under the same conditions 3-bromopropyltriethoxysilane and dipotassium trisulfide (K₂S₃) in the molar ratio of 2 to 1 were reacted to recover 3,3'-bis (triethoxysilylpropyl) trisulfide.

Instead of the triethoxysilanes used in examples 5 and 6 there also can be used as starting materials with advantage the trimethoxysilanes as well as the tripropoxy and analogous higher alkoxysilanes with up to 8 carbon atoms as well as mixed alkyl, cycloalkyl, phenyl alkoxy silanes, etc.

EXAMPLE 7

A solution of 0.5 mole of (CH₃O)₃Si —(CH₂)₃SH in 300 ml of petroleum ether (B.P. 50° to 70°C.) gradually were treated at room temperature and while leading nitrogen through the reaction solution with a solution of 0.25 mole of SCl₂ in 100 ml of petroleum ether (B.P. 50° to 70°C.). After end of the addition of the SCl₂ the mixture was heated to boiling at reflux with the passing through the nitrogen until HCl development no longer took place (about 90 minutes). After the distillative removal of the organic solvent there remained 106 grams (100% of theory of the compound of the formula (CH₃O)₃Si — (CH₂)₃— (CH₂)₃ — Si(OCH₃)₃ as the distillation sump.

| Analytical values: | C | H | Si | S |
|---|---|---|---|---|
| calculated | 34.09 | 7.15 | 13.29 | 22.75 |
| found | 33.97 | 7.03 | 12.94 | 23.08 |

EXAMPLE 8

A solution of 0.5 mole of (C₂H₅O)₃Si —(CH₂)₃SH in 300 ml of petroleum ether (B.P. 50° to 70°C.) at room temperature and with the passing of nitrogen through the reaction solution was treated gradually with a solution of 0.25 mole of S₂Cl₂ in 100 ml of petroleum ether (B.P. 50° to 70°C.) After end of the addition the mixture was heated to boiling at reflux while passing nitrogen through until no more HCl development took place (about 90 minutes). After the distillative removal of the organic solvent there remained 134.6 grams (100% of theory) of the compound of the formula (C₂H₅O)₃Si — (CH₂)₃ — S₄— (CH₂)₃ — Si(OC₂H₅)₃ as the distillation sump.

| Analytical values: | C | H | Si | S |
|---|---|---|---|---|
| calculated | 40.11 | 7.84 | 10.42 | 23.79 |
| found | 40.25 | 7.80 | 10.43 | 23.09 |

EXAMPLE 9

0.5 mole of (CH₃O)₃Si — (CH₂)₃SH and 500 ml of dimethyl sulfoxide were heated at 100°C. for 18 hours while passing nitrogen through the reaction solution. Finally excess dimethyl sulfoxide and 3-mercaptopropyl-trimethoxysilane were removed by distillation in a vacuum. In the distillation sump there remained 76 grams (77.5% of theory) of the compound of the formula (CH₃O)₃Si — (CH₂)₃ — S — S — (CH₂)₃ — Si(OCH₃)₃

| Analytical value: | | | | |
|---|---|---|---|---|
| calculated | 36.89 | 7.74 | 14.37 | 16.41 |
| found | 36.36 | 7.64 | 14.50 | 16.11 |

EXAMPLE 10

0.5 mole of (C₄H₉O)₃Si — (CH₂)₃SH and 500 ml of dimethyl sulfoxide were heated at 110°C. for 24 hours while passing nitrogen through the reaction solution. After this time the reaction was practically completed which was evidenced by the only very weakly noticeable odor of the last traces of dimethyl sulfide. Finally excess dimethyl sulfoxide and 3-mercaptopropyl tri-n-butoxysilane were removed by distillation in a vacuum. In the distillation sump there remained 121 grams (72% of theory) of the compound of the formula

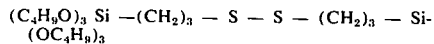

| Analytical values: | C | H | Si | S |
|---|---|---|---|---|
| calculated | 56.02 | 10.34 | 8.73 | 9.97 |
| found | 55.89 | 10.12 | 8.85 | 10.05 |

What is claimed is:

1. A compound having the formula Z — alk — $S_n$ — alk — Z, in which Z is

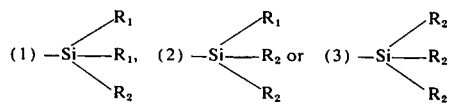

wherein $R_1$ is alkyl of 1 to 4 carbon atoms or phenyl and $R_2$ is ethoxy or cycloalkoxy with 5 to 8 carbon atoms, alk is a divalent hydrocarbon of 2 to 18 carbon atoms and $n$ is an integer of 3 to 6.

2. A compound according to claim 1 wherein alk is a saturated aliphatic hydrocarbon, unsaturated aliphatic hydrocarbon or cycloaliphatic hydrocarbon group.

3. A compound according to claim 2 wherein alk has 2 to 6 carbon atoms.

4. A compound according to claim 3 wherein alk is a saturated aliphatic hydrocarbon group of 2 to 3 carbon atoms and $n$ is an integer of 3 to 4.

5. A compound having the formula

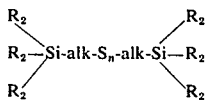

wherein $R_2$ is ethoxy or cycloalkoxy with 5 to 8 carbon atoms, alk is a divalent hydrocarbon of 1 to 18 carbon atoms and $n$ is an integer of 3 to 6.

6. A compound according to claim 5 wherein alk is a saturated aliphatic hydrocarbon, unsaturated aliphatic hydrocarbon or cycloaliphatic hydrocarbon group.

7. A compound according to claim 6 wherein alk is a saturated aliphatic hydrocarbon group of 1 to 6 carbon atoms.

8. A compound according to claim 7 wherein alk has 2 to 3 carbon atoms and $n$ is an integer of 3 to 4.

9. A compound according to claim 7 wherein all $R_2$ groups are ethoxy.

10. A compound according to claim 9 which is 3,3'-bis(triethoxysilylpropyl)tetrasulfide.

11. A compound according to claim 9 which is 3,3'-bis(triethoxysilylpropyl)trisulfide.

12. A compound according to claim 9 wherein $n$ is an integer from 3 to 4.

13. A compound according to claim 7 wherein $n$ is an integer from 3 to 4.

14. A compound according to claim 13 wherein alk is —($CH_2$)—$_3$.

15. A compound according to claim 1 where $n$ is an integer of 3 to 4.

16. A compound having the formula Z-alk-$S_n$-alk-Z in which Z is

where $R_1$ alkyl of 1 to 4 carbon atoms or phenyl and $R_2$ is alkoxy of 1 to 8 carbon atoms or cycloalkoxy with 5 to 8 carbon atoms, alk is a divalent hydrocarbon of 2 to 18 carbon atoms and $n$ is an integer of 3 to 6.

17. A compound having the formula Z-alk-$S_n$-alk-Z in which Z is

where $R_1$ is alkyl of 1 to 4 carbon atoms or phenyl and $R_2$ is alkoxy of 1 to 8 carbon atoms or cycloalkoxy with 5 to 8 carbon atoms, alk is a divalent hydrocarbon of 2 to 18 carbon atoms and $n$ is an integer of 3 to 6.

18. A compound having the formula

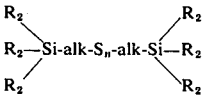

wherein $R_2$ is propoxy, alk is a divalent hydrocarbon of 1 to 18 carbon atoms and $n$ is an integer of 3 to 6.

19. A compound according to claim 18 which is 2,2'-bis(tripropoxysilyethyl)pentasulfide.

20. A compound having the formula

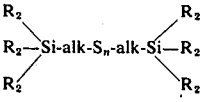

wherein $R_2$ is butoxy, alk is a divalent hydrocarbon of 1 to 18 carbon atoms and $n$ is an integer of 2 to 6.

21. A compound according to claim 20 which is 3,3'-bis(tributoxysilylpropyl)disulfide.

22. A compound according to claim 20 which is 3,3'-bis(tri t-butoxysilylpropyl)disulfide.

23. A compound according to claim 1 where $n$ is 3.

24. A compound according to claim 1 where $n$ is 4.

25. A compound according to claim 1 where $n$ is 5.

26. A compound according to claim 1 where $n$ is 6.

27. A compound having the formula Z-alk-$S_n$-alk-Z in which Z is

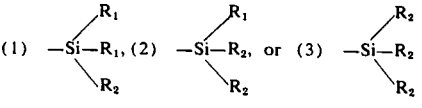

wherein $R_1$ is alkyl of 1 to 4 carbon atoms or phenyl and $R_2$ is alkoxy of 1 to 8 carbon atoms or cycloalkoxy with 5 to 8 carbon atoms, alk is a divalent hydrocarbon of 2 to 18 carbon atoms and $n$ is an integer of 3 to 6.

28. A compound according to claim 27 wherein Z is (3).

* * * * *